United States Patent
Kitamoto

(10) Patent No.: US 8,851,120 B2
(45) Date of Patent: Oct. 7, 2014

(54) FLUID HANDLING APPARATUS AND FLUID HANDLING SYSTEM

(75) Inventor: Ken Kitamoto, Saitama (JP)

(73) Assignee: Enplas Corporation, Saitama (JP)

( * ) Notice: Subject to any disclaimer, the term of this patent is extended or adjusted under 35 U.S.C. 154(b) by 373 days.

(21) Appl. No.: 13/450,889

(22) Filed: Apr. 19, 2012

(65) Prior Publication Data

US 2012/0266974 A1  Oct. 25, 2012

(30) Foreign Application Priority Data

Apr. 21, 2011  (JP) .................. 2011-095081

(51) Int. Cl.
- *G01N 27/00* (2006.01)
- *B01L 7/00* (2006.01)
- *G01N 27/447* (2006.01)
- *B01L 3/00* (2006.01)

(52) U.S. Cl.
CPC .......... *G01N 27/44791* (2013.01); *B01L 7/525* (2013.01); *B01L 2300/1805* (2013.01); *B01L 2300/0887* (2013.01); *B01L 2300/0816* (2013.01); *B01L 3/502715* (2013.01); *B01L 3/502707* (2013.01); *B01L 2400/0421* (2013.01)
USPC .......................................... 137/833; 422/503

(58) Field of Classification Search
CPC ............. B01L 3/502715; B01L 7/525; B01L 3/502707; B01L 2300/0887; B01L 2300/1805; B01L 2400/0421; B01L 2300/0816; G01N 27/44791

USPC ............ 137/833; 422/503; 156/292; 204/601
See application file for complete search history.

(56) References Cited

U.S. PATENT DOCUMENTS

| | | | |
|---|---|---|---|
| 6,284,113 B1 * | 9/2001 | Bjornson et al. | 204/601 |
| 6,939,451 B2 | 9/2005 | Zhao et al. | |
| 7,607,455 B2 * | 10/2009 | Furukawa et al. | 137/833 |
| 8,506,908 B2 * | 8/2013 | Benn et al. | 422/554 |
| 2006/0216203 A1 * | 9/2006 | Fuller et al. | 422/102 |
| 2008/0233011 A1 * | 9/2008 | Gundel et al. | 422/99 |
| 2009/0020327 A1 * | 1/2009 | Hiwada | 174/264 |
| 2009/0074623 A1 * | 3/2009 | Park et al. | 422/100 |

FOREIGN PATENT DOCUMENTS

JP  2005-127771  5/2005

\* cited by examiner

*Primary Examiner* — Eric Keasel
(74) *Attorney, Agent, or Firm* — Washida IP Group, LLC

(57) ABSTRACT

Chip body 130 in which a through hole or concave is formed, intermediate film 140, on one surface of which adhesive layer 150' is formed and lower film 170, on one surface of which transfer function layer 160 is formed, are prepared. Intermediate film 140 and lower film 170 are bonded together such that transfer function layer 160 is embedded in adhesive layer 150' to form a laminated body. The laminated body and chip body 130 are bonded together by thermocompression to manufacture micro-chip 100.

4 Claims, 16 Drawing Sheets

FLUID HANDLING APPARATUS AND FLUID HANDLING SYSTEM

CROSS REFERENCE TO RELATED APPLICATIONS

This application is entitled and claims the benefit of Japanese Patent Application No. 2011-095081, filed on Apr. 21, 2011, the disclosure of which including the specification, drawings and abstract is incorporated herein by reference in its entirety.

TECHNICAL FIELD

The present invention relates to a fluid handling apparatus and a fluid handling system provided therewith used for an analysis, processing or the like of a fluid sample.

BACKGROUND ART

In recent years, micro-analytical systems are used to carry out an analysis of trace substances such as proteins, nucleic acids (e.g., DNA) accurately and at high speed in the scientific field such as biochemistry and analytical chemistry or medical field.

An example of such micro-analytical systems is a system that performs electrophoresis using a micro-channel chip provided with a fine channel. After introducing a buffer solution and a sample into the channel of the micro-channel chip, this system performs electrophoresis on the sample. Reservoirs (concave) are formed at both ends of the channel, and the buffer solution and sample are introduced from these reservoirs into the channel. After introducing the buffer solution and sample, electrode rods are inserted into these two reservoirs and a voltage is applied to between the electrodes. Such a micro-channel chip is generally manufactured by bonding a film to a chip body in which a micro-groove (channel) and through holes (reservoirs) are formed.

As described above, in the conventional micro-channel chip, electrophoresis is performed with electrode rods being inserted in reservoirs. However, with the conventional micro-channel chip, when the electrode rod is inserted into the reservoir, there is a possibility that the buffer solution and sample may be contaminated. Furthermore, with the conventional micro-channel chip, the electrode rod needs to be inserted into the reservoir every time electrophoresis is performed. Thus, the conventional micro-channel chip involves problems of contamination and complexity of work.

In order to solve such problems, a micro-channel chip with an electrode layer arranged in a reservoir or channel is proposed (e.g., see Patent Literatures 1 and 2). For example, Patent Literature 1 discloses a micro-channel chip in which reservoirs are formed at both ends of the channel and electrode layers are arranged in these two reservoirs. These two electrode layers are connected to respective terminals outside the reservoirs. Therefore, electrophoresis can be performed by connecting external electrodes to these terminals without inserting the electrode rods into the reservoirs.

Patent Literature 1: U.S. Pat. No. 6,939,451
Patent Literature 2: Japanese Patent Application Laid-Open No. 2005-127771

According to the techniques described in Patent Literatures 1 and 2, a metal thin film or conductive ink layer is formed on a film bonded to a chip body to thereby form an electrode layer. After this, a micro-channel chip is manufactured by bonding the film on which the electrode layer is formed to the chip body.

FIG. 1A is a cross-sectional view for illustrating a conventional method of manufacturing a micro-channel chip including an electrode layer. As shown in FIG. 1A, the micro-channel chip is manufactured by bonding chip body 20 in which micro-groove 10 is formed to film 40 on which electrode layer 30 is formed by thermocompression.

However, using such a manufacturing method may produce gap 50 around electrode layer 30 due to the thickness of electrode layer 30 as shown in FIG. 1B. When gap 50 is produced around electrode layer 30, the liquid in the reservoir or channel may be leaked to the outside, posing a safety problem.

The chip body and film may be thermocompressed at a high temperature as means for preventing the occurrence of a gap. However, when thermocompression is performed at a high temperature, film 40 making up the bottom face of the channel may be deformed as shown in FIG. 1C. When film 40 is deformed in this way, the cross section of the channel changes and it is no longer possible to make an analysis with high accuracy.

Furthermore, the method of thermocompressing the chip body and film involves a problem that because the material of chip body 20 (e.g., resin) is different from the material of electrode layer 30 (e.g., carbon ink), the adherence between chip body 20 and electrode layer 30 is poor.

On the other hand, another means of bonding the chip body and film may be bonding using an adhesive. However, when an adhesive is used for bonding, adhesive 60 may stick out and the cross-sectional area of the channel may also change as shown in FIG. 1D.

As described so far, it is difficult for the prior arts to manufacture such a fluid handling apparatus (e.g., micro-channel chip) provided with a transfer function layer (e.g., electrode layer) that the size and shape of channels or reservoirs are accurately controlled and there is no gap around the transfer function layer.

It is an object of the present invention to provide a fluid handling apparatus provided with a transfer function layer for transferring electricity or heat, in which the size and shape of channels or reservoirs are accurately controlled and there is no gap around the transfer function layer. Furthermore, it is another object of the present invention to provide a fluid handling system including this fluid handling apparatus.

SUMMARY OF THE INVENTION

In order to attain the above-described object, a fluid handling apparatus according to the present invention includes: a substrate; an intermediate film having a hole, the intermediate film joined to one surface of the substrate; a lower film arranged over the intermediate film; a transfer function layer for transferring electricity or heat, the transfer function layer formed on the lower film so as to cover part of a surface of the lower film, the surface joined to the intermediate film; and a bonding layer arranged between the intermediate film and the lower film and between the intermediate film and the transfer function layer, the bonding layer bonding the intermediate film and the lower film, and the intermediate film and the transfer function layer together, wherein a through hole or concave constituting a first region is formed in the substrate at a portion corresponding to one end of the transfer function layer, an opening of the through hole or concave on the lower film side communicates with the hole of the intermediate film and is closed by the lower film, a second region communicating with an outside is formed at a portion corresponding to the other end of the transfer function layer, the transfer function layer electrically or thermally connects the first region and the second region, and the transfer function layer is arranged between the bonding layer and the lower film, the transfer function layer being in contact with the bonding layer without any gap.

A fluid handling system according to the present invention includes the above-described fluid handling apparatus.

The present invention can provide a fluid handling apparatus that prevents a liquid from leaking out of the channel or reservoir and controls the size and shape of the channel or reservoir with high accuracy. Use of the fluid handling apparatus according to the present invention makes it possible to perform an analysis or processing or the like on a sample accurately and safely.

DETAILED DESCRIPTION OF PREFERRED EMBODIMENTS

Hereinafter, embodiments of the present invention will be described in detail with reference to the accompanying drawings. As a typical example of a fluid handling apparatus of the present invention, a "micro-(channel) chip" will be described below.

The "film" in the present specification means a thin flat member. For example, the "resin film" includes not only a resin thin film but also a resin thin plate.

Embodiment 1

Embodiment 1 will describe a micro-chip that can perform heat treatment on a liquid such as reagent and liquid sample.

[Configuration of Micro-Chip]

Figure 2A:
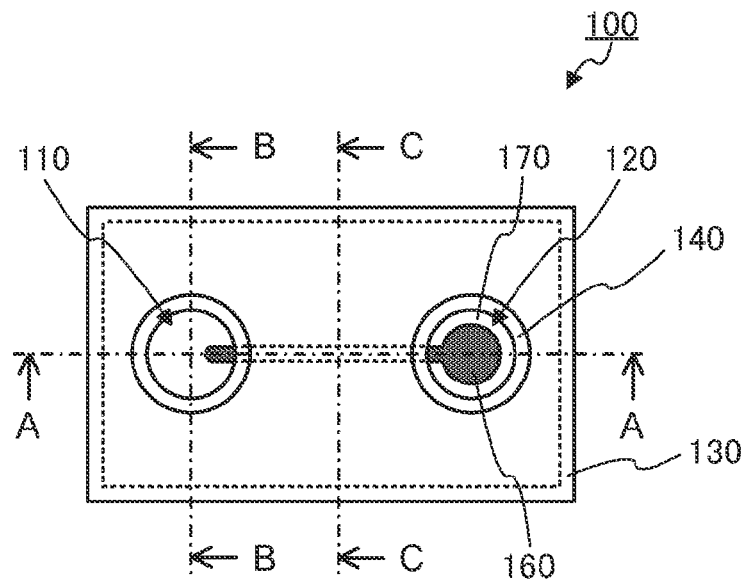
FIG. 2A is a plan view of a micro-chip of Embodiment 1.
Figure 2B:
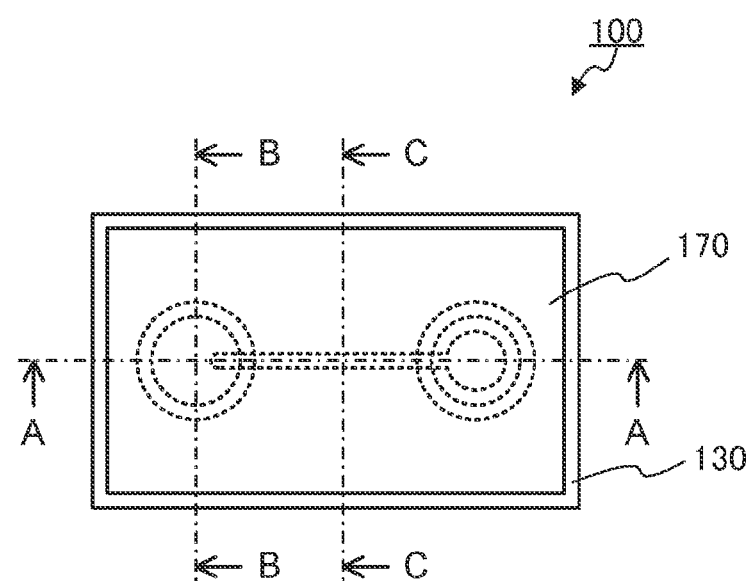
FIG. 2B is a bottom view of the micro-chip of Embodiment 1.
Figure 3A:
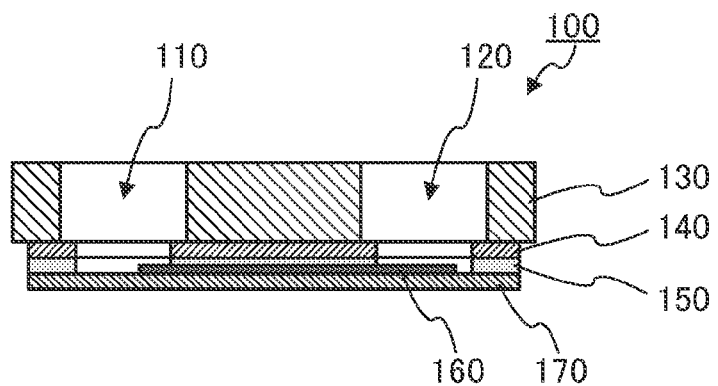
FIG. 3A is a cross-sectional view along line A-A of the micro-chip shown in FIG. 2A.
Figure 3B:
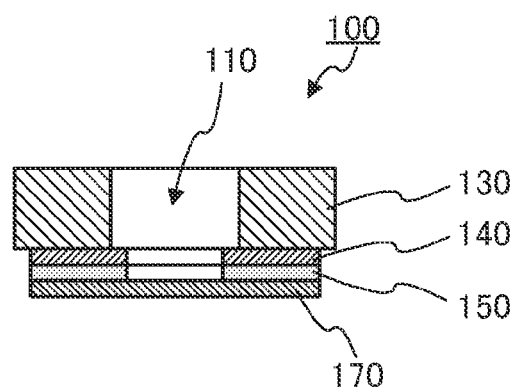
FIG. 3B is a cross-sectional view along line B-B of the micro-chip shown in FIG. 2A.
Figure 3C:
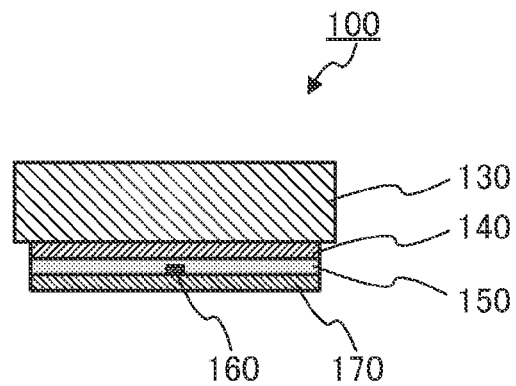
FIG. 3C is a cross-sectional view along line C-C of the micro-chip shown in FIG. 2A.

FIG. 2 and FIG. 3 are diagrams illustrating a configuration of a micro-chip of Embodiment 1. FIG. 2A is a plan view and FIG. 2B is a bottom view. Furthermore, FIG. 3A is a cross-sectional view along line A-A shown in FIG. 2A and FIG. 2B, FIG. 3B is a cross-sectional view along line B-B and FIG. 3C is a cross-sectional view along line C-C.

As shown in FIG. 2A and FIG. 3A, micro-chip 100 is a tabular device having two bottomed concaves. As will be described later, one concave functions as first region 110 that is provided a liquid such as a reagent and liquid sample. The other concave functions as second region 120 in which an electric heater is inserted (see FIG. 4).

As shown in FIG. 2A and FIG. 3A, micro-chip 100 has chip body (substrate) 130, intermediate film 140, bonding layer 150, heat conductive layer (transfer function layer) 160 and lower film 170.

Figure 6A:
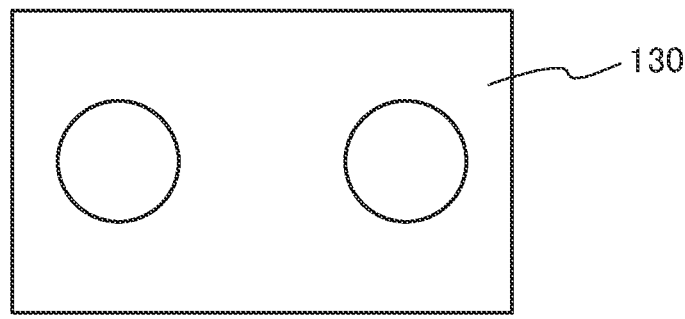
FIG. 6A is a plan view of a chip body of the micro-chip of Embodiment 1.

Chip body 130 is a transparent, substantially rectangular resin substrate and has two through holes (see FIG. 6A). The two through holes become bottomed concave (first region 110 and second region 120) when lower film 170 closes the opening on the intermediate film 140 side (see FIG. 3A). The shape of the through hole is not particularly limited, and is, for example, substantially columnar. The thickness of chip body 130 is not particularly limited, and, for example, 1 mm to 10 mm. Furthermore, the diameter of the through hole is not particularly limited, and is, for example, on the order of 2 mm.

The type of resin making up chip body (substrate) 130 is not particularly limited, and can be selected from publicly known resin according to the use as appropriate. Examples of the resin making up chip body 130 include polyethylene terephthalate, polycarbonate, polymethylmethacrylate, vinyl chloride, polypropylene, polyether, polyethylene or the like.

Intermediate film 140 is a transparent, substantially rectangular resin film bonded to one surface of chip body 130. Intermediate film 140 is bonded to chip body 130, for example, by thermocompression. Intermediate film 140 has two through holes at positions corresponding to the two through holes of chip body 130 (see FIG. 6B). That is, the through holes of chip body 130 communicate with the through holes of intermediate film 140. The thickness of intermediate film 140 is not particularly limited, and is, for example, on the order of 100 μm. Furthermore, the diameter of the through hole is not particularly limited, and is, for example, on the order of 1.8 mm.

The type of resin making up intermediate film 140 is not particularly limited, and can be selected from publicly known resin according to the use as appropriate. Examples of resin making up intermediate film 140 are the same as those of resin making up chip body 130. The resin making up intermediate film 140 is preferably the same as the resin making up chip body 130 from the perspective of improving the adherence between chip body 130 and intermediate film 140.

Bonding layer 150 is a layer arranged between intermediate film 140 and lower film 170 and between intermediate film 140 and heat conductive layer 160. Bonding layer 150 bonds intermediate film 140 and lower film 170. Furthermore, bonding layer 150 bonds intermediate film 140 and heat conductive layer 160.

As shown in FIG. 3C, the thickness of bonding layer 150 may differ between the region not contacting heat conductive layer 160 (region directly contacting lower film 170) and the region contacting heat conductive layer 160. For example, the thickness of bonding layer 150 in the region not contacting heat conductive layer 160 may be a thickness substantially the same as the sum of the thickness of heat conductive layer 160 and the thickness of bonding layer 150 on the heat conductive layer 160. As a result, the distance between intermediate film 140 and lower film 170 is substantially constant irrespective of the presence or absence of heat conductive layer 160. The thickness of bonding layer 150 in the region not contacting heat conductive layer 160 is not particularly limited as long as it is greater than the thickness of heat conductive layer 160, and is, for example, on the order of 20 μm.

As will be described later, bonding layer 150 is formed by hardening an adhesive. The type of the adhesive used to form bonding layer 150 is not particularly limited as long as it has heat-resistance and its peeling strength after hardening is strong.

Heat conductive layer (transfer function layer) 160 is arranged between bonding layer 150 and lower film 170. Examples of heat conductive layer 160 include a metal thin film or the like. One end of heat conductive layer 160 is exposed in first region 110 and the other end is exposed in second region 120 (see FIG. 2A and FIG. 3A). Heat conductive layer 160 thermally connects first region 110 and second region 120. The thickness of heat conductive layer 160 is not particularly limited, and is, for example, on the order of 10 μm.

Figure 1A:
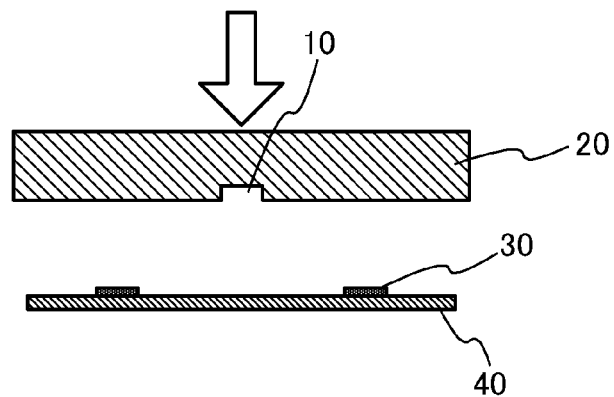
FIG. 1A is a cross-sectional view for illustrating a conventional micro-channel chip manufacturing method.
Figure 1B:
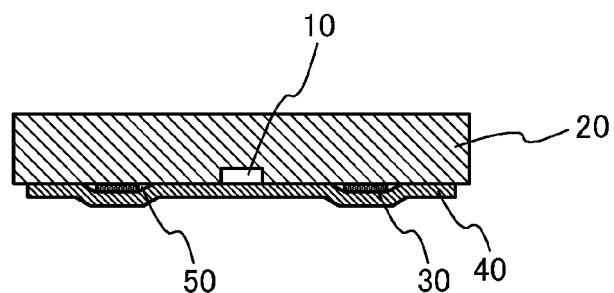
FIG. 1B to FIG. 1D are cross-sectional views for illustrating problems of the conventional micro-channel chip manufacturing method.
Figure 1C:
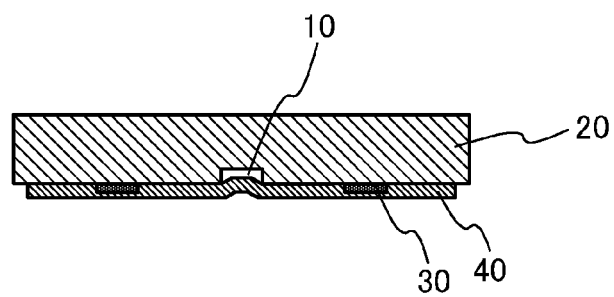
Figure 1D:
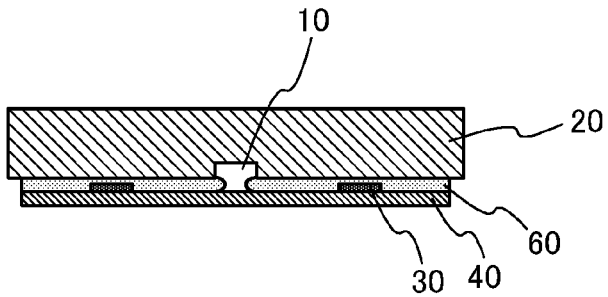

As shown in FIG. 3C, heat conductive layer 160 is arranged between bonding layer 150 and lower film 170 while in contact with bonding layer 150 without any gap. For example, heat conductive layer 160 is arranged between bonding layer 150 and lower film 170 while being embedded in bonding layer 150. The periphery of heat conductive layer 160 is filled with bonding layer 150 and no gap exists around heat conductive layer 160 (see FIG. 1B and FIG. 3C for comparison).

Lower film 170 is a transparent, substantially rectangular resin film bonded to intermediate film 140 via bonding layer 150. As described above, lower film 170 closes one opening of the through hole of chip body 130. The thickness of lower film 170 is not particularly limited, and is, for example, on the order of 100 μm.

The type of resin making up lower film 170 is not particularly limited, and can be selected from publicly known resin according to the use as appropriate. Examples of resin making up lower film 170 are the same as examples of resin making up chip body 130. The type of resin making up lower film 170 may be the same as or may be different from the type of resin making up chip body 130 or intermediate film 140.

[Method of Use of Micro-Chip]

Figure 4:
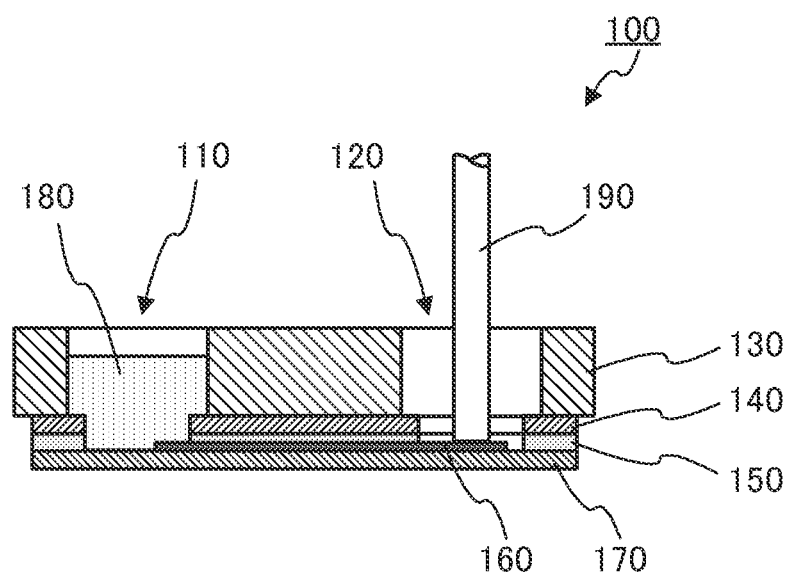
FIG. 4 is a cross-sectional view for illustrating a mode of use of the micro-chip of Embodiment 1.

FIG. 4 is a cross-sectional view for illustrating a mode of use of micro-chip 100 of Embodiment 1. As shown in FIG. 4, liquid 180 such as a reagent or liquid sample is supplied to first region 110 of micro-chip 100. Furthermore, electric heater 190 is inserted into second region 120 of micro-chip 100. Electric heater 190 contacts heat conductive layer 160. When electric heater 190 is heated in this condition, heat is transmitted from second region 120 to first region 110 via heat conductive layer 160 and liquid 180 is heated. At this time, since there is no gap around heat conductive layer 160 (see FIG. 3C), liquid 180 in first region 110 does not leak out to the second region 120 side.

[Method of Manufacturing Micro-Chip]

Next, the method of manufacturing micro-chip 100 of Embodiment 1 will be described with reference to FIG. 5 and FIG. 6.

Figure 5A:
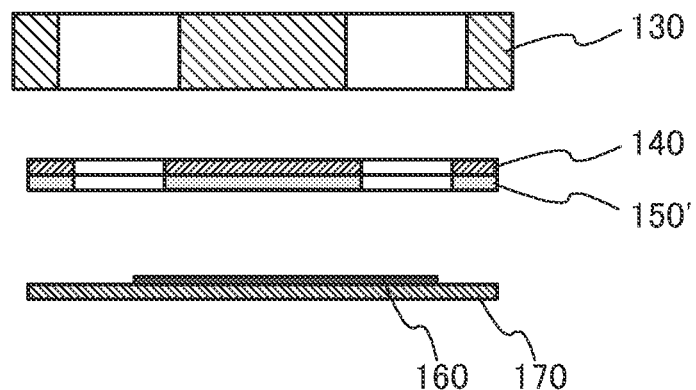
FIG. 5A to FIG. 5C are cross-sectional views for illustrating manufacturing steps of the micro-chip of Embodiment 1.
Figure 6B:
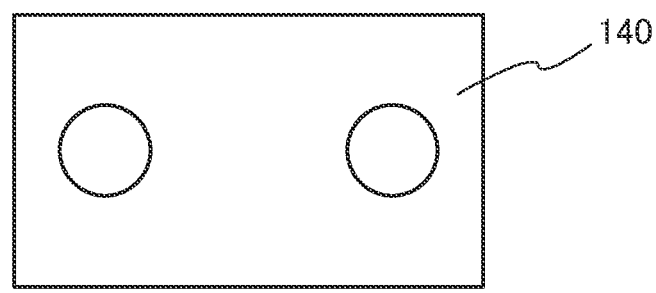
FIG. 6B is a plan view of an intermediate film of the micro-chip of Embodiment 1.
Figure 6C:
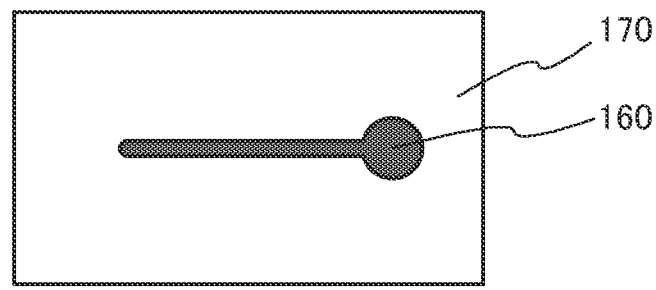
FIG. 6C is a plan view of a lower film of the micro-chip of Embodiment 1.

First, chip body 130, intermediate film 140 on which adhesive layer 150' (layer made of an adhesive before hardening) is formed and lower film 170 on which heat conductive layer 160 is formed are prepared as shown in FIG. 5A. For example, intermediate film 140 on which adhesive layer 150' is formed can be obtained by applying an adhesive to one surface of intermediate film 140. Furthermore, lower film 170 on which heat conductive layer 160 is formed can be obtained by forming a metal thin film on one surface of lower film 170 in a predetermined pattern. FIG. 6A is a plan view of chip body 130, FIG. 6B is a plan view of intermediate film 140 (surface on which adhesive layer 150' is not formed) and FIG. 6C is a plan view of lower film 170 (surface on which heat conductive layer 160 is formed).

Figure 5B:
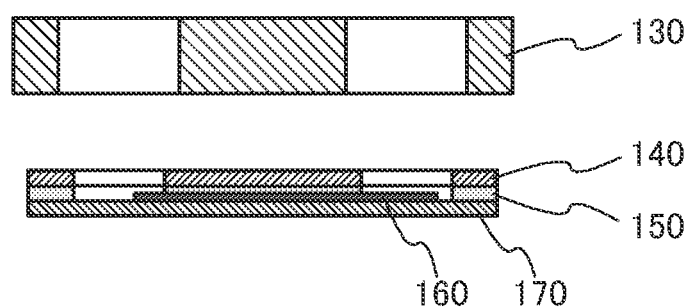

Next, as shown in FIG. 5B, intermediate film 140 and lower film 170 on which heat conductive layer 160 is formed are bonded together via adhesive layer 150'. This makes it possible to obtain a laminated body made up of intermediate film 140, bonding layer 150, heat conductive layer 160 and lower film 170. Since the shape of the adhesive before hardening can be freely changed, heat conductive layer 160 formed on lower film 170 comes into contact with bonding layer 150 without any gap (see FIG. 3C).

Figure 5C:
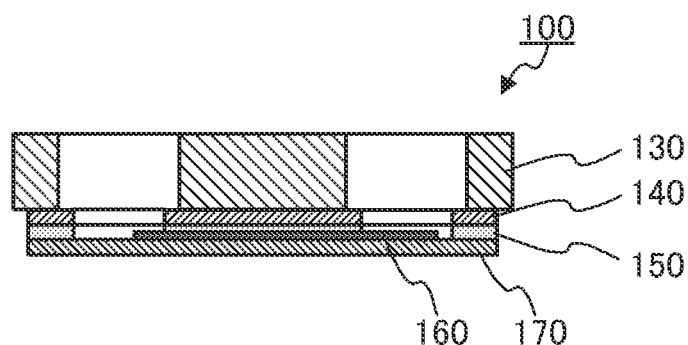

Finally, as shown in FIG. 5C, chip body 130 and the laminated body including intermediate film 140 and lower film 170 are bonded together by thermocompression and micro-chip 100 is formed. Since there is no gap around heat conductive layer 160, there is no need to perform thermocompression at too a high temperature. Therefore, intermediate film 140 and lower film 170 will never be deformed.

Before bonding chip body 130 and the laminated body (intermediate film 140, bonding layer 150, heat conductive layer 160 and lower film 170), it is preferable to form an alignment mark (not shown) on the surface to be bonded of chip body 130 and the surface to be bonded of lower film 170. Forming the alignment mark on the surface of chip body 130 and the surface of lower film 170 makes it easier to align chip body 130 with the laminated body. Regarding chip body 130, the alignment mark can be easily formed when molding chip body 130. Regarding lower film 170, an alignment mark can be easily formed simultaneously with the formation of heat conductive layer 160 on lower film 170.

[Effects]

In micro-chip 100 of Embodiment 1, intermediate film 140 and lower film 170 or heat conductive layer 160 are firmly bonded together by the bonding layer without any gap. Furthermore, since there is no member made of a different material such as metal between chip body 130 and intermediate film 140, chip body 130 and intermediate film 140 are also firmly bonded together without any gap. Therefore, with micro-chip 100 of Embodiment 1, a liquid supplied to first region 110 never leaks to second region 120 or the outside.

Figure 7:
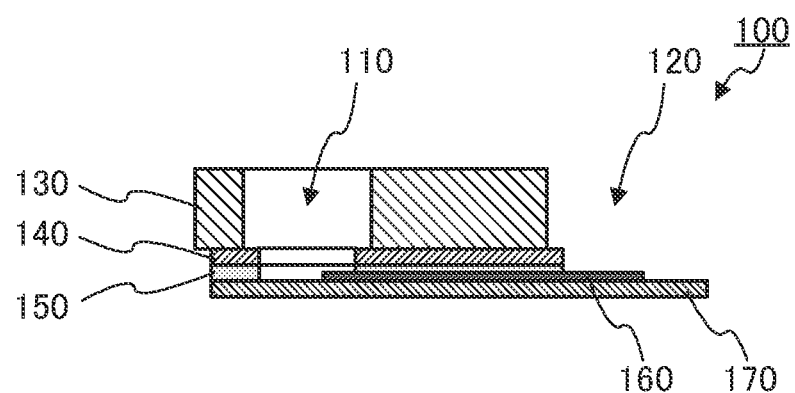
FIG. 7 is a cross-sectional view of another example of the micro-chip of Embodiment 1.

Although a case has been described so far where the end of heat conductive layer 160 on the second region 120 side is arranged within the through hole of chip body 130, the end of heat conductive layer 160 on the second region 120 side may not necessarily be arranged within the through hole of chip body 130. That is, as shown in FIG. 7, the end of transfer function layer 160 on the second region 120 side may also be directly exposed to the outside.

Embodiment 2

Embodiment 2 will describe a micro-channel chip that can perform electrophoresis.

[Configuration of Micro-Channel Chip]

Figure 8A:
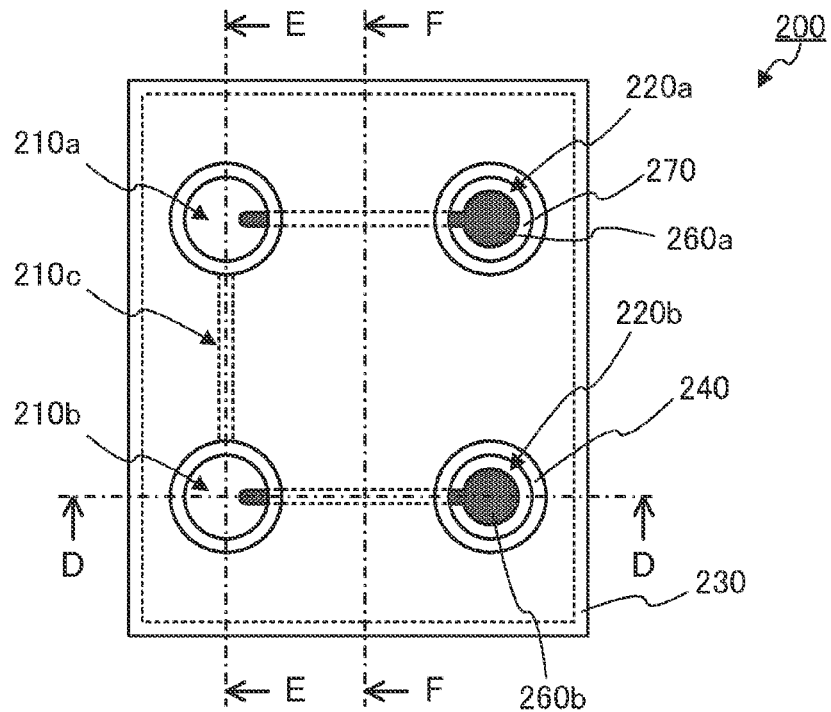
FIG. 8A is a plan view of a micro-channel chip of Embodiment 2.
Figure 8B:
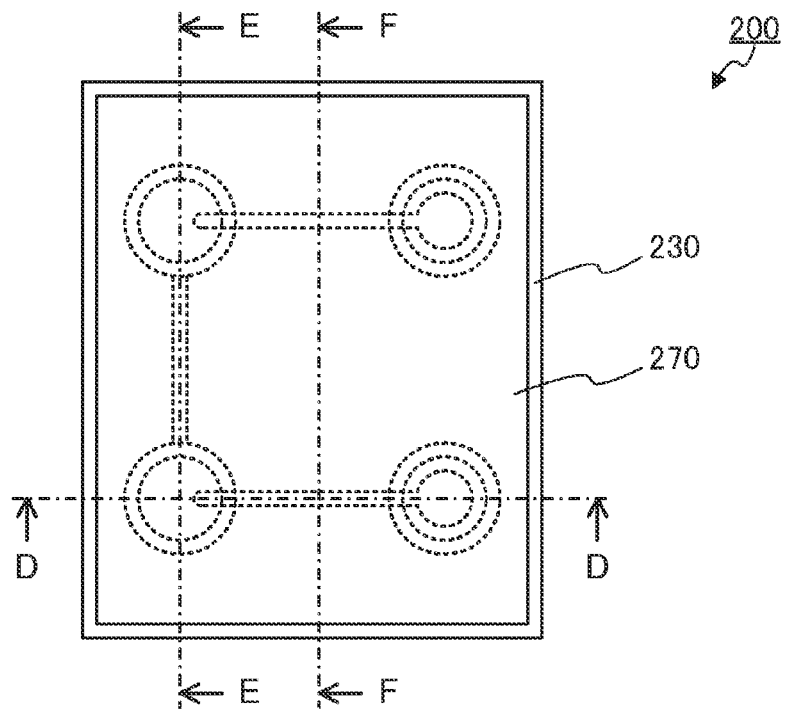
FIG. 8B is a bottom view of the micro-channel chip of Embodiment 2.
Figure 9A:
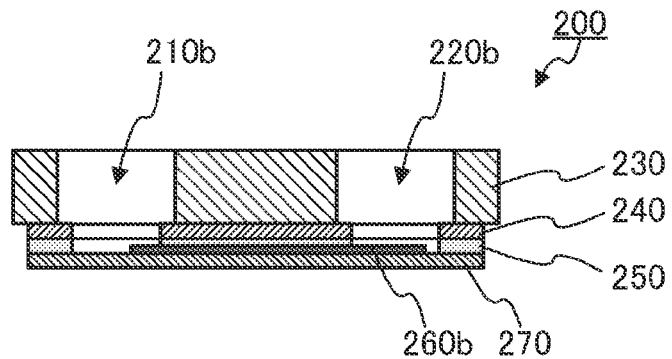
FIG. 9A is a cross-sectional view along line D-D of the micro-channel chip shown in FIG. 8A.
Figure 9B:
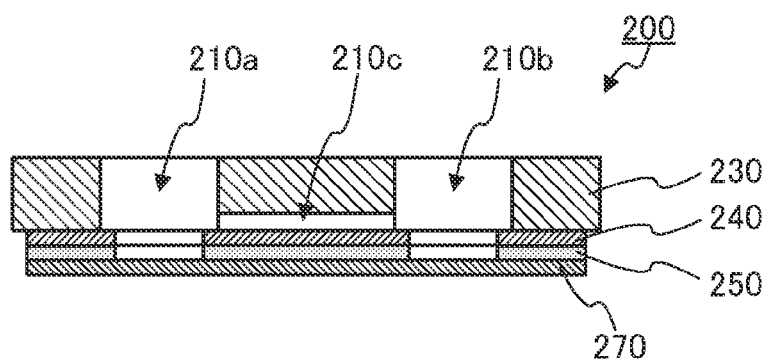
FIG. 9B is a cross-sectional view along line E-E of the micro-channel chip shown in FIG. 8A.
Figure 9C:
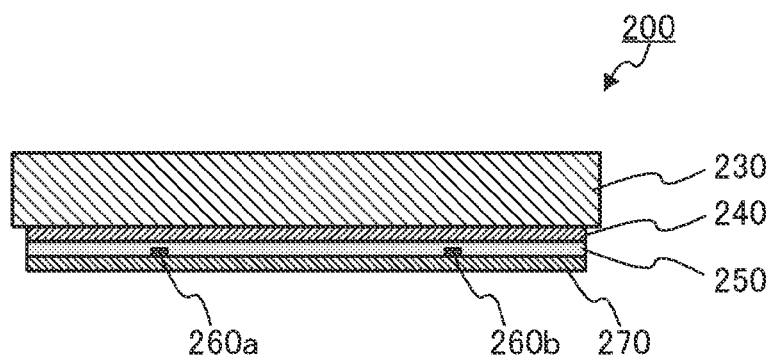
FIG. 9C is a cross-sectional view along line F-F of the micro-channel chip shown in FIG. 8A.

FIG. 8 and FIG. 9 are diagrams illustrating a configuration of the micro-channel chip of Embodiment 2. FIG. 8A is a plan view and FIG. 8B is a bottom view. Furthermore, FIG. 9A is a cross-sectional view along line D-D shown in FIG. 8A and FIG. 8B, FIG. 9B is a cross-sectional view along line E-E and FIG. 9C is a cross-sectional view along line F-F.

As shown in FIG. 8A, micro-channel chip 200 is a tabular device including four bottomed concaves. As will be described later, two concaves are connected together via channel 210c and function as first regions 210a and 210b used to supply and remove a liquid to/from channel 210c respectively. Furthermore, the remaining two concaves function as second regions 220a and 220b into which electrode rods are inserted (see FIG. 10).

Micro-channel chip 200 of Embodiment 2 is different from micro-chip 100 of Embodiment 1 in that micro-channel chip 200 is provided with four bottomed concaves, a channel connecting between concaves and an electrical conductive layer as a transfer function layer. Thus, micro-channel chip 200 will be described focused on these points. The material and thickness or the like of each component are the same as those of micro-chip 100 of Embodiment 1.

As shown in FIG. 8A and FIG. 9A, micro-channel chip 200 includes chip body (substrate) 230, intermediate film 240, bonding layer 250, electrical conductive layers (transfer function layers) 260a and 260b, and lower film 270.

Figure 11A:
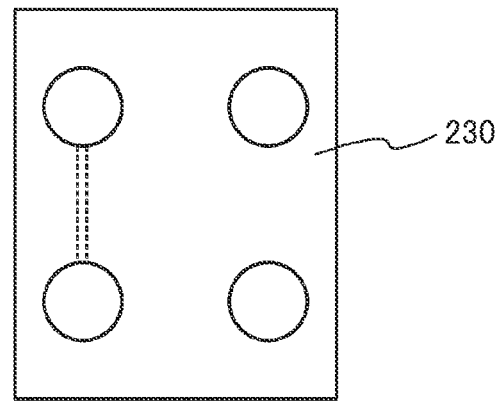
FIG. 11A is a plan view of a chip body of the micro-channel chip of Embodiment 2.

Chip body 230 is a transparent, substantially rectangular resin substrate and includes four through holes (see FIG. 11A). The four through holes constitute bottomed concaves (first regions 210a and 210b, and second regions 220a and 220b) when openings on the intermediate film 240 side are closed by lower film 270.

Furthermore, a micro-groove that connects the through hole that forms first region 210a and the through hole that forms first region 210b is formed on the surface of chip body 230 on the intermediate film 240 side (see FIG. 11A). This micro-groove constitutes channel 210c that connects first region 210a and first region 210b when the opening is closed by intermediate film 240 (see FIG. 9B). The cross-sectional shape of the micro-groove is not particularly limited, and is, for example, substantially a rectangle having a length of each side (width and depth) of on the order of several tens of µm.

Intermediate film 240 is a transparent, substantially rectangular resin film bonded to the surface in which the micro-groove of chip body 230 is formed. Intermediate film 240 includes four through holes at positions corresponding to the through holes of chip body 230 (see FIG. 11B). That is, the through holes of chip body 230 communicate with the through holes of intermediate film 240. On the other hand, there is no through hole at a position corresponding to the micro-groove of chip body 230. Therefore, intermediate film 240 functions as a bottom face of channel 210c (see FIG. 9B).

Bonding layer 250 is a layer arranged between intermediate film 240 and lower film 270 or electrical conductive layers 260a and 260b. Bonding layer 250 bonds intermediate film 240 and lower film 270, and intermediate film 240 and electrical conductive layers 260a and 260b.

Electrical conductive layers (transfer function layers) 260a and 260b are conductive layers arranged between bonding layer 250 and lower film 270. Examples of electrical conductive layers 260a and 260b include a conductive ink layer (e.g., carbon ink layer) and metal thin film. One end of electrical conductive layer 260a is exposed in first region 210a and the other end is exposed in second region 220a. Similarly, one end of electrical conductive layer 260b is exposed in first region 210b and the other end is exposed in second region 220b (see FIG. 8A). Electrical conductive layer 260a electrically connects first region 210a and second region 220a. Similarly, electrical conductive layer 260b electrically connects first region 210b and second region 220b. Electrical conductive layers 260a and 260b are arranged between bonding layer 250 and lower film 270 while in contact with bonding layer 250 without any gap (see FIG. 9C). For example, electrical conductive layers 260a and 260b are arranged between bonding layer 250 and lower film 270 while being embedded in bonding layer 250.

Lower film 270 is a transparent, substantially rectangular resin film bonded to intermediate film 240 via bonding layer 250. As described above, lower film 270 closes one of the two openings of each of the through holes of chip body 230.

[Method of Use of Micro-Channel Chip]

Figure 10:
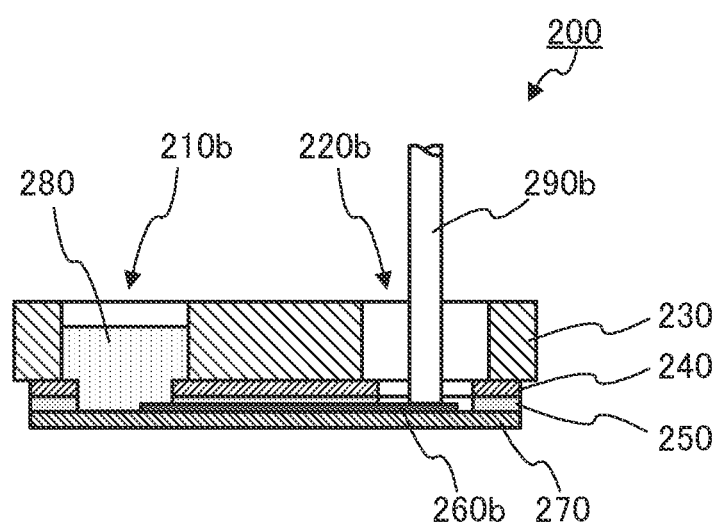
FIG. 10 is a cross-sectional view for illustrating a mode of use of the micro-channel chip of Embodiment 2.

FIG. 10 is a cross-sectional view for illustrating a mode of use of micro-channel chip 200 of Embodiment 2. As shown in FIG. 10, liquid 280 such as an electrolyte or liquid sample is supplied from first regions 210a and 210b to channel 210c. Furthermore, electrode rods 290a and 290b are inserted into second regions 220a and 220b. Electrode rods 290a and 290b contact electrical conductive layers 260a and 260b respectively. When a voltage is applied between electrode rods 290a and 290b, electrophoresis takes place in channel 210c. At this time, an electrophoresis result can be acquired in real time by measuring the intensity of fluorescence at a predetermined position of channel 210c.

[Method of Manufacturing Micro-Channel Chip]

Micro-channel chip 200 of Embodiment 2 can be manufactured using a procedure similar to that of micro-chip 100 of Embodiment 1.

Figure 11B:
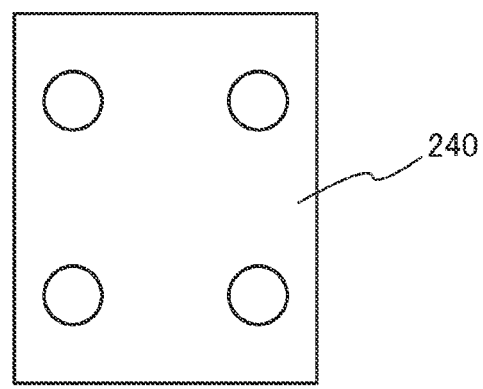
FIG. 11B is a plan view of an intermediate film of the micro-channel chip of Embodiment 2.
Figure 11C:
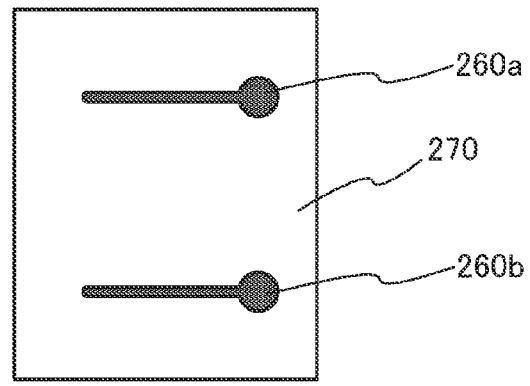
FIG. 11C is a plan view of a lower film of the micro-channel chip of Embodiment 2.

FIG. 11 is a plan view of each component used to manufacture micro-channel chip 200. FIG. 11A is a plan view of chip body 230, FIG. 11B is a plan view of intermediate film 240 (surface on which adhesive layer 250' is not formed) and FIG. 11C is a plan view of lower film 270 (surface on which electrical conductive layers 260a and 260b are formed).

Micro-channel chip 200 can be manufactured by bonding intermediate film 240 and lower film 270 together via adhesive layer 250' and then bonding the laminated body and chip body 230 by thermocompression. At this time, since intermediate film 240 exists between chip body 230 and adhesive layer 250', the size and shape of channel 210c are never changed by influences of adhesive layer 250'.

[Effect]

With micro-channel chip 200 of Embodiment 2, the liquid supplied to first regions 210a and 210b, and channel 210c does not leak to second regions 220a and 220b or outside as in the case of micro-chip 100 of Embodiment 1. Furthermore, since the size and shape of channel 210c do not change in manufacturing steps, the size and shape of channel 210c can be controlled accurately.

Figure 12:
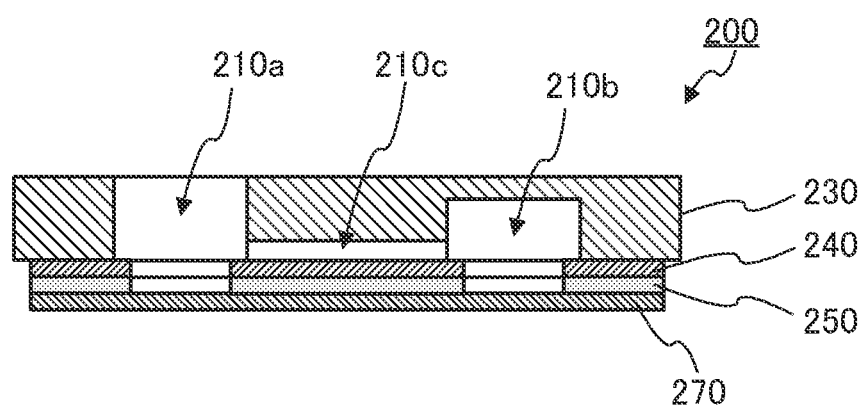
FIG. 12 is a cross-sectional view of another example of the micro-channel chip of Embodiment 2.

A case has been described so far as an example where both of two first regions 210a and 210b have an opening, but one of two first regions 210a and 210b may not have any opening. That is, as shown in FIG. 12, if first region 210a has an opening, first region 210b need not have any opening. In this case, a through hole is formed in a region corresponding to first region 210a of chip body 230. On the other hand, a concave having an opening on the surface on the intermediate film 240 side is formed in a region corresponding to first region 210b of chip body 230. An air hole communicating with first region 210b may also be formed to make it easier to introduce a liquid into channel 210c.

Furthermore, as in the case of micro-chip 100 of Embodiment 1 shown in FIG. 7, ends of electrical conductive layers 260a and 260b on the second regions 220a and 220b sides may be directly exposed to the outside.

Embodiment 3

Embodiment 3 will describe a micro-channel chip capable of performing electrophoresis and having a detection window for measuring intensity of fluorescence more accurately.

[Configuration of Micro-Channel Chip]

Figure 13A:
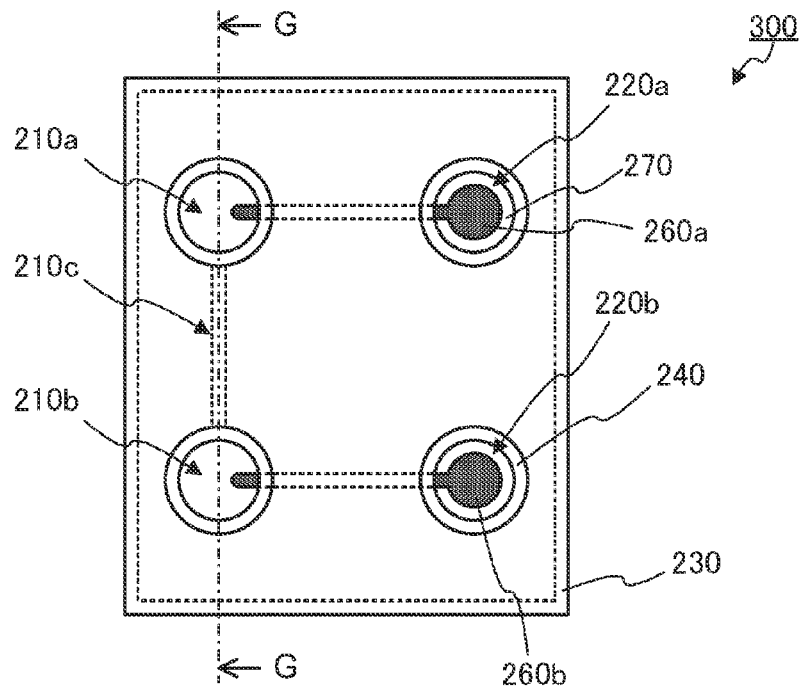
FIG. 13A is a plan view of a micro-channel chip of Embodiment 3.
Figure 13B:
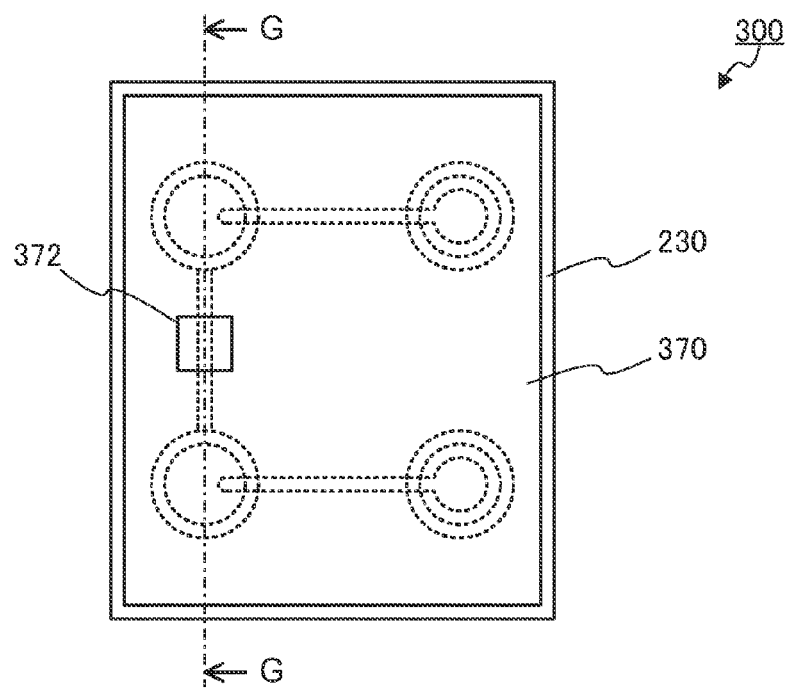
FIG. 13B is a bottom view of the micro-channel chip of Embodiment 3.
Figure 14:
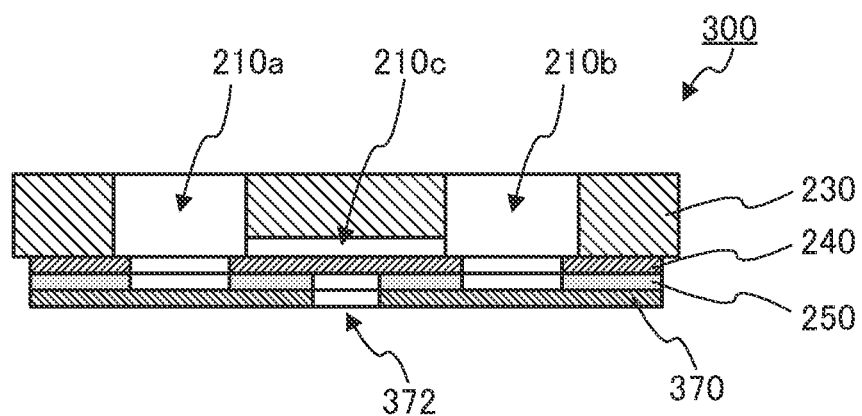
FIG. 14 is a cross-sectional view along line G-G of the micro-channel chip shown in FIG. 13A.

FIG. 13 and FIG. 14 are diagrams illustrating a configuration of a micro-channel chip according to Embodiment 3. FIG. 13A is a plan view and FIG. 13B is a bottom view. Furthermore, FIG. 14 is a cross-sectional view along line G-G shown in FIG. 13A and FIG. 13B.

Micro-channel chip 300 according to Embodiment 3 is different from micro-channel chip 200 according to Embodiment 2 in that a through hole (detection window) is provided in the lower film. Thus, the same components as those of micro-channel chip 200 in Embodiment 2 will be assigned the same reference numerals and descriptions thereof will be omitted.

As shown in FIG. 13A and FIG. 14, micro-channel chip 300 includes chip body (substrate) 230, intermediate film 240, bonding layer 250, electrical conductive layers (transfer function layers) 260a and 260b, and lower film 370.

Lower film 370 is a transparent, substantially rectangular resin film bonded to intermediate film 240 via bonding layer 230. Lower film 370 closes one of the two openings of each of the through holes of chip body 230. Lower film 370 includes through hole 372 at a position corresponding to a microgroove of chip body 230 (see FIG. 13B and FIG. 16C).

[Method of Use of Micro-Channel Chip]

Figure 15:
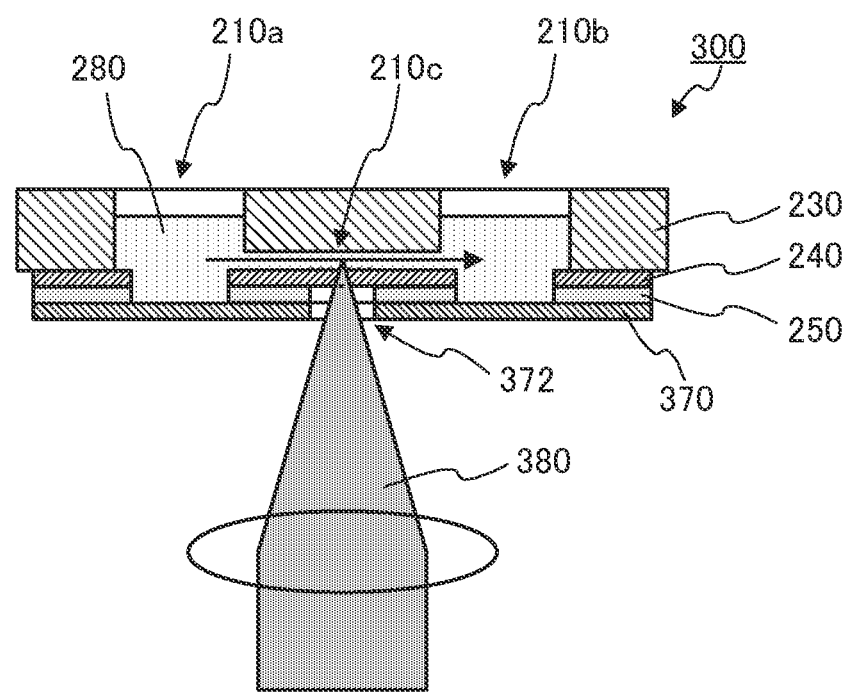
FIG. 15 is a cross-sectional view for illustrating a mode of use of the micro-channel chip of Embodiment 3.

FIG. 15 is a cross-sectional view for illustrating a mode of use of micro-channel chip 300 of Embodiment 3. As shown in FIG. 15, liquid 280 including an electrolyte or sample is supplied from first regions 210a and 210b into channel 210c. Furthermore, electrode rods 290a and 290b are inserted into second regions 220a and 220b respectively. When a voltage is applied to electrode rods 290a and 290b in this condition, electrophoresis takes place in channel 210c (see an arrow in the figure). At the same time, excitation light 380 is radiated from the lower film 370 side of micro-channel chip 300 at a predetermined detection position of channel 210c and the intensity of fluorescence at the position is measured in real time. Thus, an electrophoresis result can be acquired in real time by measuring the intensity of fluorescence of a substance which is migrating in channel 210c.

Since all intermediate film 240, bonding layer 250 and lower film 370 contain resin, auto fluorescence may be generated which becomes noise when measuring the intensity of fluorescence. Since through hole 372 is provided in lower film 370 in micro-channel chip 300 of Embodiment 3, excitation light 380 and fluorescent light (not shown) pass through only intermediate film 240, and pass through neither bonding layer 250 nor lower film 370. Therefore, use of micro-channel chip 300 of Embodiment 3 makes it possible to suppress influences of auto fluorescence and measure the intensity of fluorescence more accurately.

[Method of Manufacturing Micro-Channel Chip]

Micro-channel chip 300 according to Embodiment 3 can be manufactured using a procedure similar to that of micro-channel chip 200 of Embodiment 2.

Figure 16A:
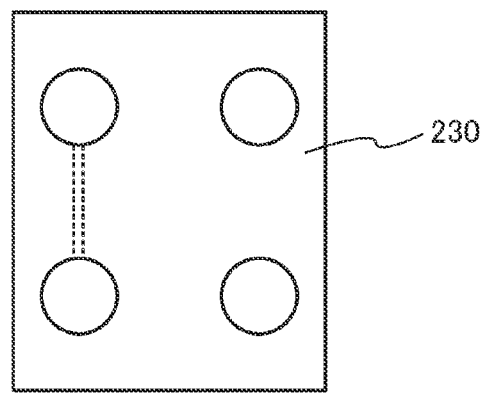
FIG. 16A is a plan view of a chip body of the micro-channel chip of Embodiment 3.
Figure 16B:
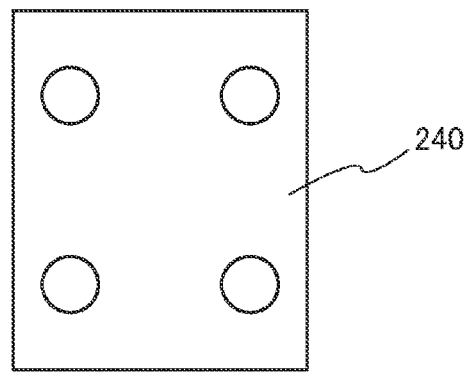
FIG. 16B is a plan view of an intermediate film of the micro-channel chip of Embodiment 3.
Figure 16C:
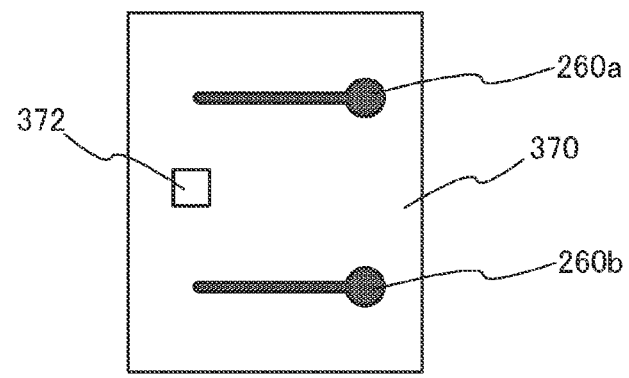
FIG. 16C is a plan view of a lower film of the micro-channel chip of Embodiment 3.

FIG. 16 is a plan view of each component used when manufacturing micro-channel chip 300. FIG. 16A is a plan view of chip body 230, FIG. 16B is a plan view of intermediate film 240 (surface on which adhesive layer 250' is not formed) and FIG. 16C is a plan view of lower film 370 (surface on which electrical conductive layers 260a and 260b are formed).

Micro-channel chip 300 can be manufactured by bonding intermediate film 240 and lower film 370 together via adhesive layer 250' and then bonding the laminated body and chip body 230 together by thermocompression as in the case of micro-channel chip 200 of Embodiment 2.

The fluid handling apparatus of the present invention is useful as a micro-chip or micro-channel chip used, for example, in the scientific field and medical field. Furthermore, the fluid handling system of the present invention is useful as a system that analyzes trace substances with high accuracy and at a high speed.

What is claimed is:

1. A fluid handling apparatus comprising:
a substrate;
an intermediate film having a hole, said intermediate film being joined to one surface of the substrate;
a lower film arranged over the intermediate film;
a transfer function layer for transferring electricity or heat, the transfer function layer being formed on the lower film so as to cover a part of a surface of the lower film on a side of the intermediate film; and
a bonding layer arranged between the intermediate film and the lower film and between the intermediate film and the transfer function layer for bonding the intermediate film and the lower film, and the intermediate film and the transfer function layer together,
wherein said substrate includes a through hole or a concave constituting a first region formed at a portion corresponding to one end of the transfer function layer,
said through hole or said concave includes an opening on a side of the lower film for communicating with the hole of the intermediate film, said opening being closed by the lower film,
said transfer function layer includes a second region formed at a portion corresponding to the other end thereof for communicating with an outside,
said transfer function layer is arranged to electrically or thermally connect the first region and the second region, and
said transfer function layer is arranged between the bonding layer and the lower film in a state that the transfer function layer is in contact with the bonding layer without any gap.

2. The fluid handling apparatus according to claim 1, wherein said substrate is formed of a resin substrate, and said intermediate film and the lower film are formed of resin films.

3. The fluid handling apparatus according to claim 1, wherein said transfer function layer is formed of a metal thin film or a conductive ink layer.

4. A fluid handling system comprising the fluid handling apparatus according to claim 1.

* * * * *